(12) United States Patent
Austin et al.

(10) Patent No.: US 12,429,155 B2
(45) Date of Patent: Sep. 30, 2025

(54) SLIT-FREE SAFE DISCONNECT

(71) Applicant: CareFusion 303, Inc., San Diego, CA (US)

(72) Inventors: Abin Austin, Thrissur (IN); Leah Paige Gaffney, Orange, CA (US); Kowshika K, Tirupur (IN); Ryan Callahan, Long Beach, CA (US)

(73) Assignee: CAREFUSION 303, INC., San Diego, CA (US)

( * ) Notice: Subject to any disclaimer, the term of this patent is extended or adjusted under 35 U.S.C. 154(b) by 106 days.

(21) Appl. No.: 18/329,948

(22) Filed: Jun. 6, 2023

(65) Prior Publication Data
US 2024/0410506 A1 Dec. 12, 2024

(51) Int. Cl.
| | |
|---|---|
| *F16L 37/35* | (2006.01) |
| *A61M 39/10* | (2006.01) |
| *F16L 37/34* | (2006.01) |

(52) U.S. Cl.
CPC ............ *F16L 37/35* (2013.01); *A61M 39/10* (2013.01); *F16L 37/34* (2013.01)

(58) Field of Classification Search
CPC .. A61M 2039/1027; A61M 2039/1061; A61M 39/1011; A61M 39/10; A61M 39/26; F16L 37/32; F16L 37/34; F16L 37/35; F16L 55/1015
See application file for complete search history.

(56) References Cited

U.S. PATENT DOCUMENTS

| | | | | |
|---|---|---|---|---|
| 4,946,455 A * | 8/1990 | Rosen | .................... | F16L 37/367 |
| | | | | 604/905 |
| 5,492,147 A * | 2/1996 | Challender | ............. | F16L 37/28 |
| | | | | 604/905 |
| 5,820,614 A * | 10/1998 | Erskine | ............... | F16L 55/1007 |
| | | | | 604/905 |
| 10,315,025 B2 * | 6/2019 | Phillips | .................. | A61M 39/26 |
| 10,655,768 B2 * | 5/2020 | Jones | .................... | A61M 39/24 |
| 10,850,059 B2 * | 12/2020 | Bencke | ................. | F16L 37/086 |
| 10,864,362 B2 * | 12/2020 | Jones | .................... | A61M 39/24 |
| 11,491,084 B2 * | 11/2022 | Ueda | ...................... | A61M 39/14 |
| 2008/0103487 A1 * | 5/2008 | Miyasaka | ............. | A61M 39/26 |
| | | | | 604/537 |

(Continued)

FOREIGN PATENT DOCUMENTS

| | | | |
|---|---|---|---|
| AU | 2021296923 A1 | 2/2023 | |
| WO | WO-2021263198 A1 * | 12/2021 | ............ A61M 39/10 |

OTHER PUBLICATIONS

International Search Report and Written Opinion for Application No. PCT/US2024/031469, dated Aug. 19, 2024, 12 pages.

*Primary Examiner* — David Colon-Morales
(74) *Attorney, Agent, or Firm* — MASCHOFF BRENNAN

(57) ABSTRACT

Fluid connector assemblies with fluid connectors connected via a detachable ring are disclosed. A fluid connector assembly may include a pair of fluid connectors and a ring that couples the pair of connectors. The ring may be configured to detach from either connector upon experiencing a separating force that exceeds a predetermined threshold force. The detachment of the ring may decouple the pair of fluid connectors. When the pair of fluid connectors are connected, fluid may flow between them. When the pair of fluid connectors are disconnected, fluid may not flow.

19 Claims, 6 Drawing Sheets

(56) References Cited

U.S. PATENT DOCUMENTS

| | | | |
|---|---|---|---|
| 2008/0197626 A1* | 8/2008 | Coambs | A61M 39/26 285/330 |
| 2014/0323988 A1* | 10/2014 | Magnani | A61M 39/1011 604/256 |
| 2022/0288378 A1 | 9/2022 | Mermelshtein et al. | |

* cited by examiner

SLIT-FREE SAFE DISCONNECT

FIELD OF THE INVENTION

The present disclosure generally relates to connectors, and, in particular, to connector couplings.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

One or more embodiments of the present disclosure are directed to a coupler assembly including a first connector having an outer surface and a first fluid pathway, a second connector having an exterior rim and a second fluid pathway, and a ring having a first portion and an axially offset second portion, the first portion being configured to be coupled to the outer surface of the first connector, and the second portion having a plurality of arms extending axially away from the first portion. When the ring is coupled to the first connector, and when the first and second connectors are coupled together such that the first fluid pathway is in fluid communication with the second fluid pathway, the plurality of arms are configured to detachably engage the exterior rim of the second connector to secure the coupling of the first and second connectors.

In some embodiments, each of the plurality of arms of the ring includes connecting portions which engage with the exterior rim of the second connector. The ring may be configured to detach the first connector and the second connector upon a separating force exceeding a predetermined threshold force.

In some embodiments, the outer surface of the first connector comprises an alignment detent, and the ring comprises an alignment tab, and the alignment tab is configured to be received by the alignment detent when the ring is coupled to the outer surface of the first connector.

In some embodiments, the plurality of arms of the ring is configured to detachably engage, via an interference fit, the exterior rim of the second connector.

In some embodiments, the plurality of arms and the exterior rim of the second connector are configured to detach upon a decoupling force exceeding a predetermined coupling force. In some embodiments, the ring and the first connector are configured to detach upon a decoupling force exceeding a predetermined coupling force.

In some embodiments, the separating force is applied axially along the first connector and the second connector. In some embodiments, the separating force is a resultant axial force along the coupled first connector and second connector.

In some embodiments, the first connector comprises an exterior portion and the second connector comprises an interior chamber such that the exterior portion of the first connector fits within the interior chamber of the second connector to provide fluid communication between the first and second fluid pathways.

One or more embodiments of the present disclosure are directed to a method of coupling two connectors, including providing a first connector with a first end and a second end opposite the first end, providing a second connector with an exterior rim, sliding a ring having a plurality of arms around the first connector, detachably connecting the ring to the first connector via a detent on the first connector and an engagement means on the ring, detachably connecting the ring to the second connector via the plurality of arms engaging with the exterior rim of the second connector, and forming a fluid pathway between the coupled first and second connectors.

In some embodiments, the method includes sliding the ring around the first connector from the first end. In some embodiments, the method includes sliding the ring around the first connector from the second end.

In some embodiments, the method includes detaching the first connector and the second connector with an application of a force exceeding a predetermined threshold force.

In some embodiments, detaching the first and second connectors creates a break in the fluid pathway.

One or more embodiments of the present disclosure are directed to a coupling assembly including a first connector including a first connector body having a first inlet and a first outlet in fluid communication with the first inlet and a collar sleeved over the first connector body between the first inlet and the first outlet, the collar comprising a collar body including a plurality of arms extending outward circumferentially from the collar body and a second connector including a second connector body comprising a first end and a second end in fluid communication with the first end, wherein the collar body connects to an outer surface of the first connector via a friction fit, and wherein the plurality of arms of the collar connects to an outer surface of the second connector via a friction fit.

In some embodiments, the plurality of arms of the collar further comprises an interior ridge that connects to an exterior rim of the second connector to form the friction fit.

In some embodiments, the interior ridge of the plurality of arms of the collar disengages from the exterior rim of the second connector upon an application of a force exceeding a predetermined threshold force. In some embodiments, the force exceeding a predetermined threshold force is applied such that the first connector is pulled away from the second connector.

In some embodiments, the first connector is coupled to a first portion of tubing at the first inlet, and the second connector is coupled to a second portion of tubing at the second end.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
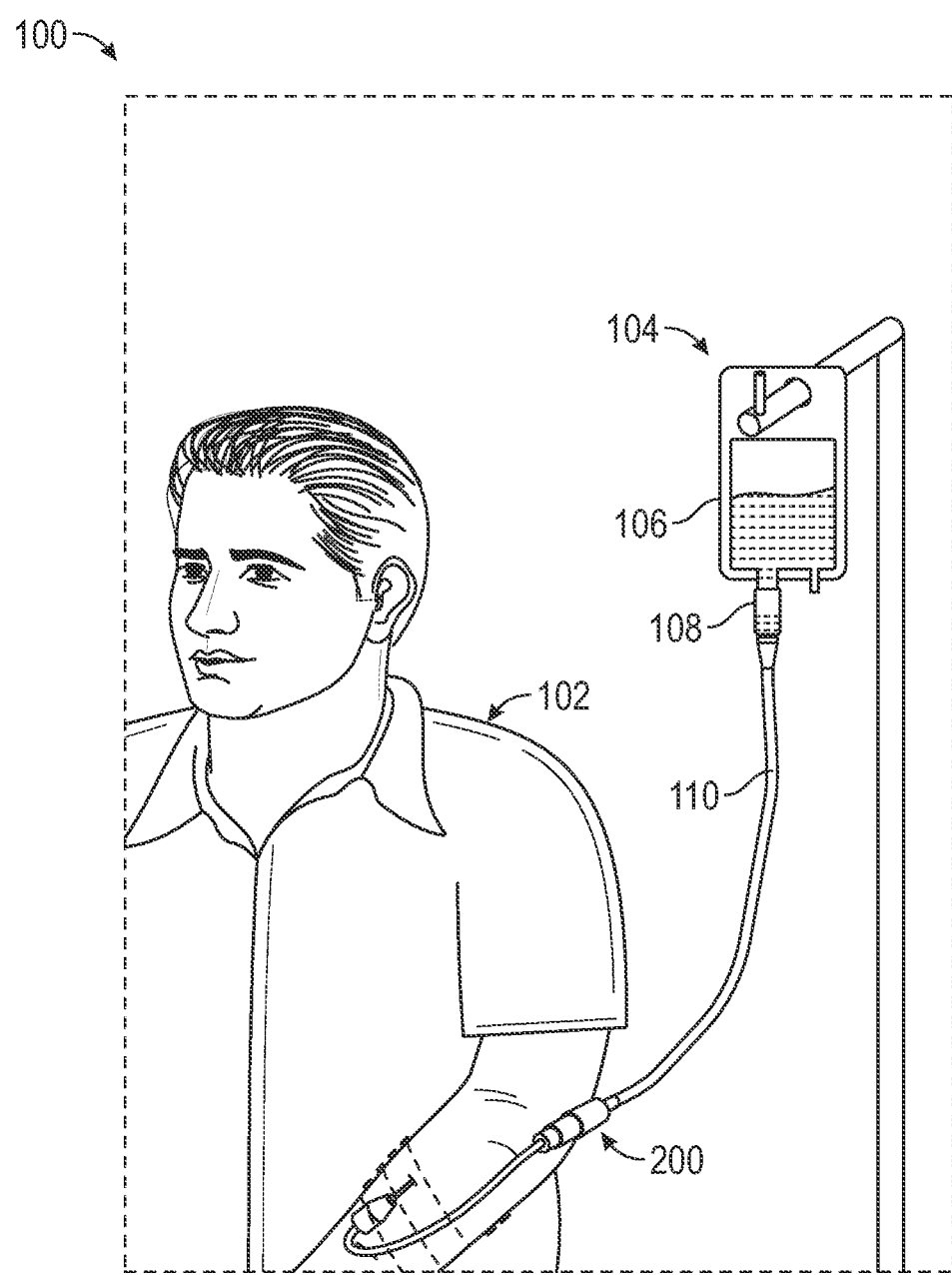
FIG. 1 is a diagram of a coupler assembly in use during delivery of intravenous (IV) fluids to a patient, in accordance with some embodiments of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

The disclosed coupler assembly overcomes several challenges discovered with respect to certain IV catheters. When a higher full force is exerted upon the catheter than the securement method was designed to withstand, it may result in catheter dislodgement. In such cases, a nurse may need to change the catheter, which causes pain to the patient and requires additional costs and time be invested by the nurse for new catheterization. Examples of such catheter dislodgement scenarios include a patient rolling over in bed or catching their IV lines on bed rails, transfers of patients to different beds, fidgeting by pediatric patients, visitors catching on the lines, and/or disoriented adult patients pulling out their lines. Because the accidental or unintentional dislodgement of tubing, catheters, or fittings may interrupt the administration of medical fluids and may cause discomfort to patients, the use of certain conventional IV lines is undesirable.

Therefore, in accordance with the present disclosure, it is advantageous to provide couplers and coupler/connector assemblies as described herein that allow for the disconnection of an IV line at the point of the coupler assembly. This disconnection point may help avoid catheter dislodgement and may provide an easy point of re-connection that is additionally easy to clean.

The disclosed coupler assembly includes a first connector, a second connector, and a ring. The ring, or collar, is configured to couple the first connector to the second connector. In some embodiments, the ring includes a first portion and an axially offset second portion, where the first portion is configured to be coupled to the outer surface of the first connector, and the second portion has a plurality of arms that extend axially away from the first portion, where the plurality of arms detachably engages with an exterior rim of the second connector to secure the two connectors together. When the first and second connectors are coupled together, a fluid pathway may exist through both the first and second connectors.

The coupler assembly may be configured to couple a first portion of tubing to a second portion of tubing. For example, the first portion of tubing may be coupled to the first connector and the second portion of tubing may be coupled to the second connector. The first portion of tubing and/or the second portion of tubing may also couple to a patient or a fluid source. In some embodiments, the coupler assembly allows for the flow of fluid from the first portion of tubing to the second portion of tubing. For example, the ring may couple the first connector to the second connector such that a fluid pathway is formed through the first connector and the second connector to allow the flow of fluid from the first portion of tubing through the first connector and the second connector to the second portion of tubing. The fluid pathway may allow for the flow of fluid from the second portion of tubing through the second connector and the first connector to the first portion of tubing.

In some embodiments, the ring includes an alignment tab, and the outer surface of the first connector includes an alignment detent. The ring may be able to slide around the first connector such that the alignment tab is able to slide into the alignment detent, coupling the ring to the first connector. In other embodiments, the ring may include a detent and the first connector may include a tab, such that the tab may make a connection with the detent that couples the ring to the first connector. In other embodiments, the ring may include a protruded edge and the first connector may include an indented portion such that the protruded edge of the ring may snap onto the indented portion of the first connector, coupling the ring and the first connector. In other embodiments, the ring may include an indented portion and the first connector may include a protruded edge, such that the first connector may snap into the ring, coupling the ring and the first connector.

In some embodiments, the ring includes at least one arm that extends axially outward from a ring-shaped portion of the ring. The arms of the ring may include a protruded portion, and the second connector may include an indented portion, such that the protruded portion of the ring may connect with or snap onto the indented portion of the second connector, coupling the ring and the second connector. In some embodiments, the second connector may include a protruded portion, and the ring may include an indented portion, such that the protruded portion of the second connector and the indented portion of the ring may connect, coupling the ring and the second connector.

In some embodiments, the ring may couple, or connect, to the first connector first, and then couple to the second connector. In some embodiments, the ring may couple to the second connector first, and then couple to the first connector. In some embodiments, the ring may couple to the first and second connectors simultaneously.

In some embodiments, the coupler assembly is configured to decoupled based on a force that exceeds a predetermined threshold force. When a force is applied to the coupler assembly, such as a pullout force, that exceeds the predetermined threshold force, the first connector may decouple from the ring and the second connector. The pullout force may be a force that occurs along the longitudinal axis of the first connector. In some embodiments, the pullout force is caused by tugging or pulling on the first portion of tubing coupled to the first connector. Alternatively, the pullout out force applied to the first connector may be caused by tugging or pulling on the second connector and/or the second portion of tubing coupled to the second connector. Alternatively, the pullout force may be a resultant force that pulls the first connector away from the second connector, such as dropping an item on the connectors or tubing.

In some embodiments, the ring may decouple from the second connector while maintaining its coupling to the first connector. In some embodiments, the ring may decouple from the first connector while maintaining its coupling to the second connector. In some embodiments, the ring may decouple from both the first and the second connectors.

In some embodiments, when the first connector is decoupled from the second connector, the fluid pathway is blocked such that fluid does not continue to flow through the first connector or through the second connector.

The ring, the first connector, and the second connector may be discarded or replaced with a new sterile component to prevent infection or contamination that can occur if the component is re-used (e.g., the first connector is coupled again to the second connector).

FIG. 1 shows an exemplary system 100 in which a patient 102 may be connected to a fluid system 104. The fluid system 104 may contain an IV fluid 106 that passes through connection point 108 into IV line 110, which is inserted into a vein of patient 102. The IV line 110 may continue through assembly 200, which, when connected, may allow the IV fluid 106 to continue through IV line 110 and into patient 102. When assembly 200 is disconnected, IV fluid 106 may not continue to flow through IV line 110 and into patient 102.

Figure 2:
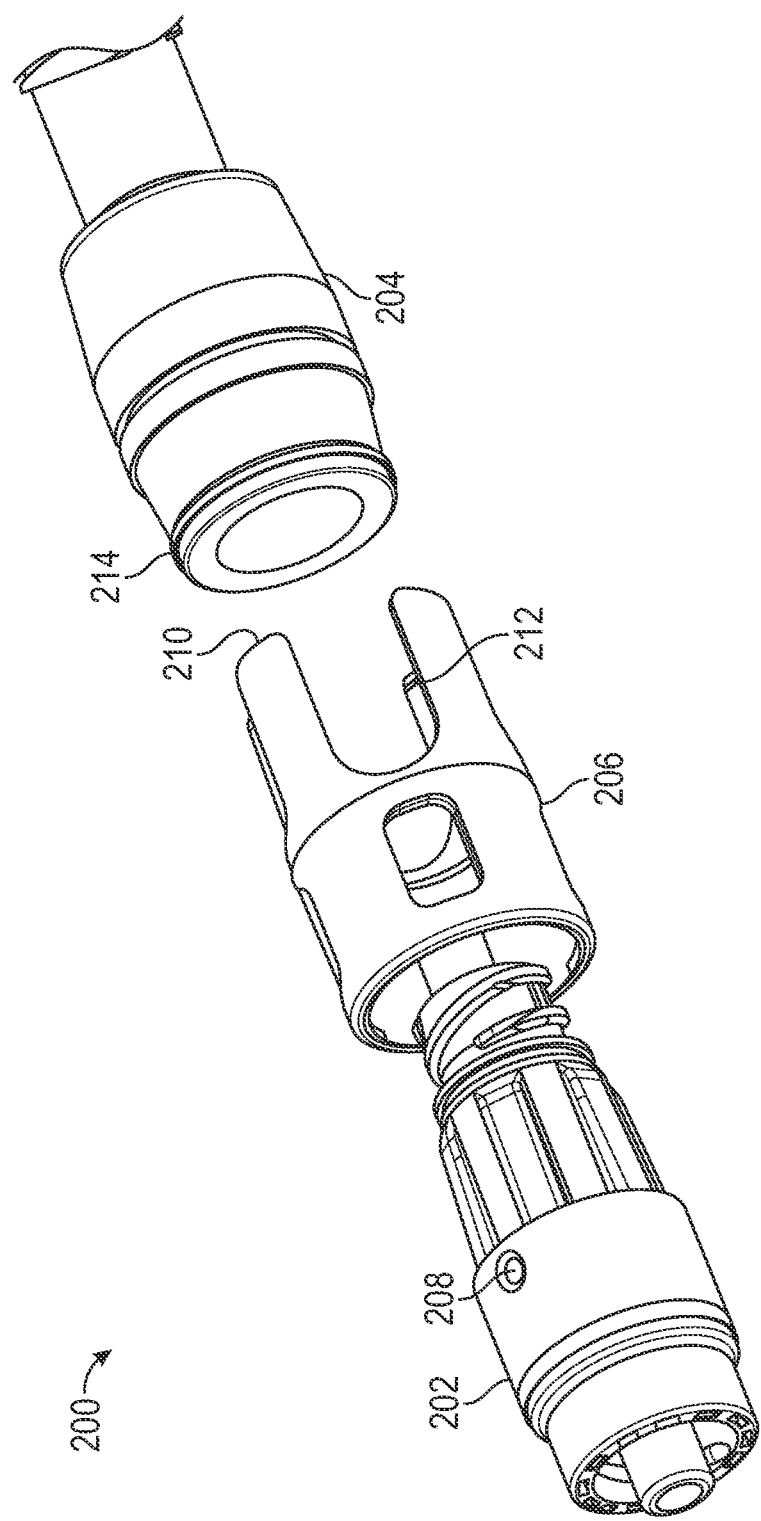
FIG. 2 shows an exploded view of a coupler assembly with a first connector, a second connector, and a ring, in accordance with some embodiments of the present disclosure.

FIG. 2 shows an exploded view of assembly 200. Assembly 200 includes first connector 202, second connector 204, and ring 206. First connector 202 may include a means such as a detent 208 for ring 206 to snap onto first connector 202. Ring 206 may include arms 210 that extend radially outward from the ring-shaped body of ring 206. These arms 210 may include protrusions 212 that can snap onto an indentation 214 on second connector 204.

In some embodiments, ring 206 may include a first portion that is substantially ring-shaped and fits circumferentially around an outer surface of first connector 202. The ring first portion may include cutouts that allow, for example, for ring 206 to more easily slide around first connector 206. Ring 206 may additionally have an axially offset second portion having a plurality of arms 210 that extend axially away from the first portion. These arms 210 may have connecting portions such as protrusions 212 that may aid in the ring 206 connecting to second connector 204, such as in snapping into indentation 214.

Figure 3:
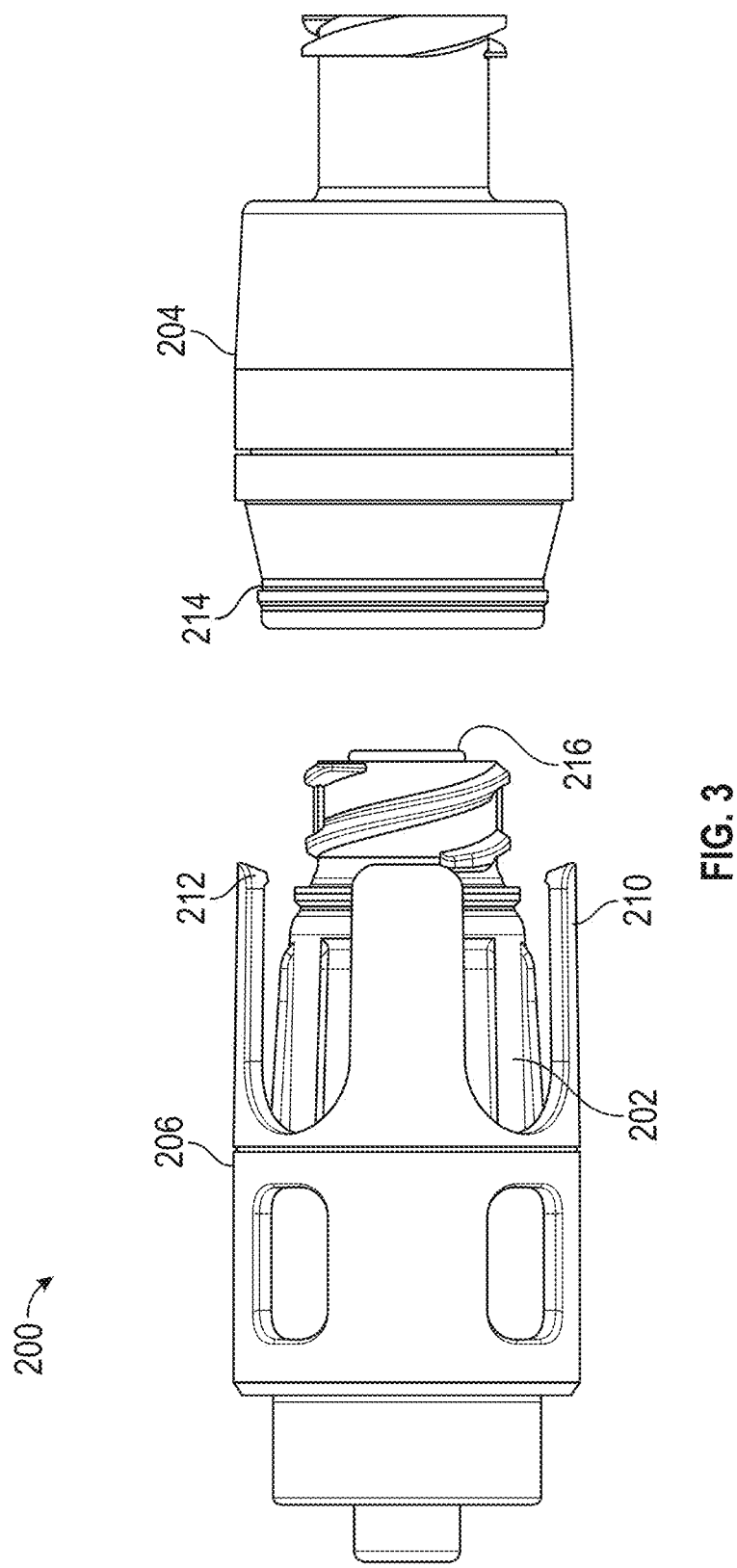
FIG. 3 shows the coupler assembly of FIG. 2 with the ring attached to the first connector, in accordance with some embodiments of the present disclosure.

FIG. 3 shows the ring 206 coupled to first connector 202. In some embodiments, the ring 206 may fit around first connector 202 such that first connector 202 continues to extend lengthwise past the ends of arms 210 of ring 206. The end of first connector 202 nearest to a connecting edge of second connector 204 may taper such that the tapered end of first connector 202 may fit within the connecting end of second connector 204. The interior portion of first connector 202 may contain a flexible valve 216 that extends to the far edge of the tapered end of first connector 202. This flexible valve may prevent fluid from flowing through first connector 202 when not coupled to second connector 204.

In some embodiments, the ring 206 fits around first connector 202 in a friction fit. In some embodiments, the ring 206 snaps around first connector 202 when an alignment tab on the interior of ring 206 fits within a detent on ring 206, such as detent 208. In some embodiments, the connection may be a combination of friction or interference fit.

Figure 4:
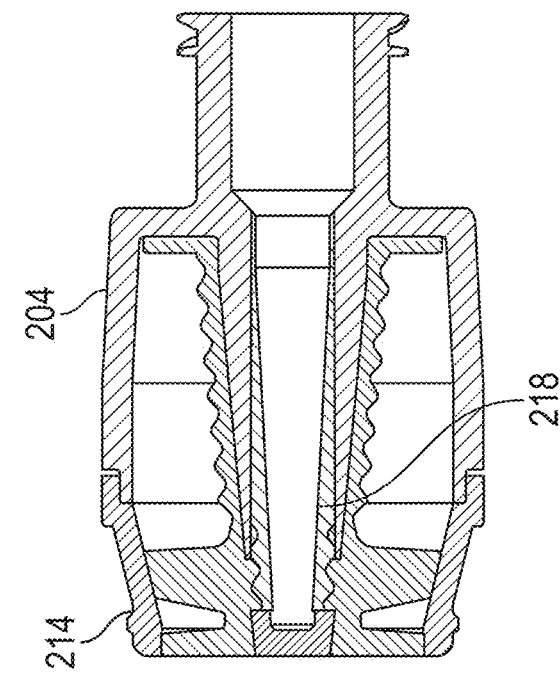
FIG. 4 shows a cross-sectional view of the coupler assembly shown in FIG. 3, in accordance with some embodiments of the present disclosure.
Figure 4:
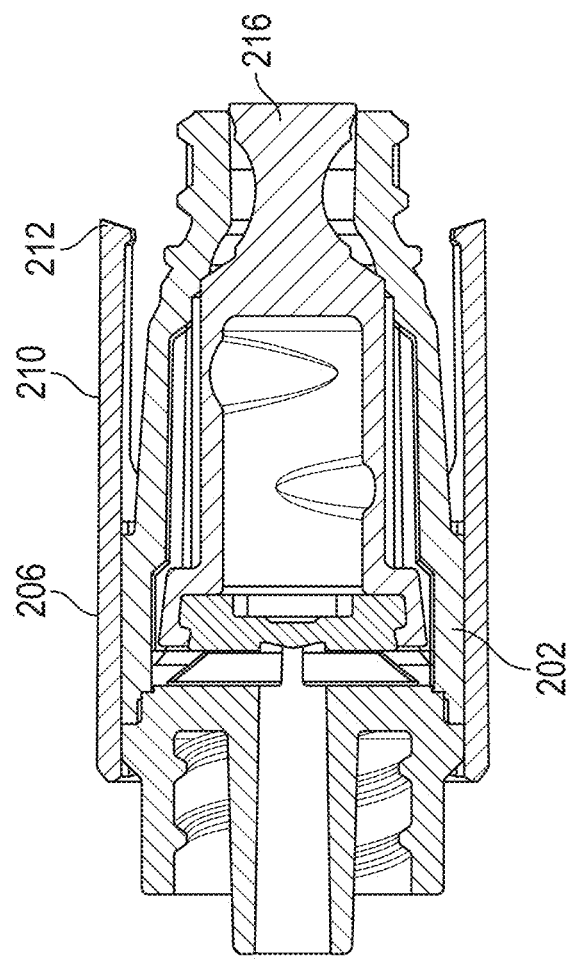

FIG. 4 shows a cross-sectional view of the coupler assembly shown in FIG. 3. In some embodiments, an interior portion of second connector 204 may include a valve 218. The interior portion of first connector 202 may include a first inlet and a first outlet in fluid communication with the first inlet. The interior portion of second connector 204 may include a first end and a second end in fluid communication with the first end.

Figure 5:
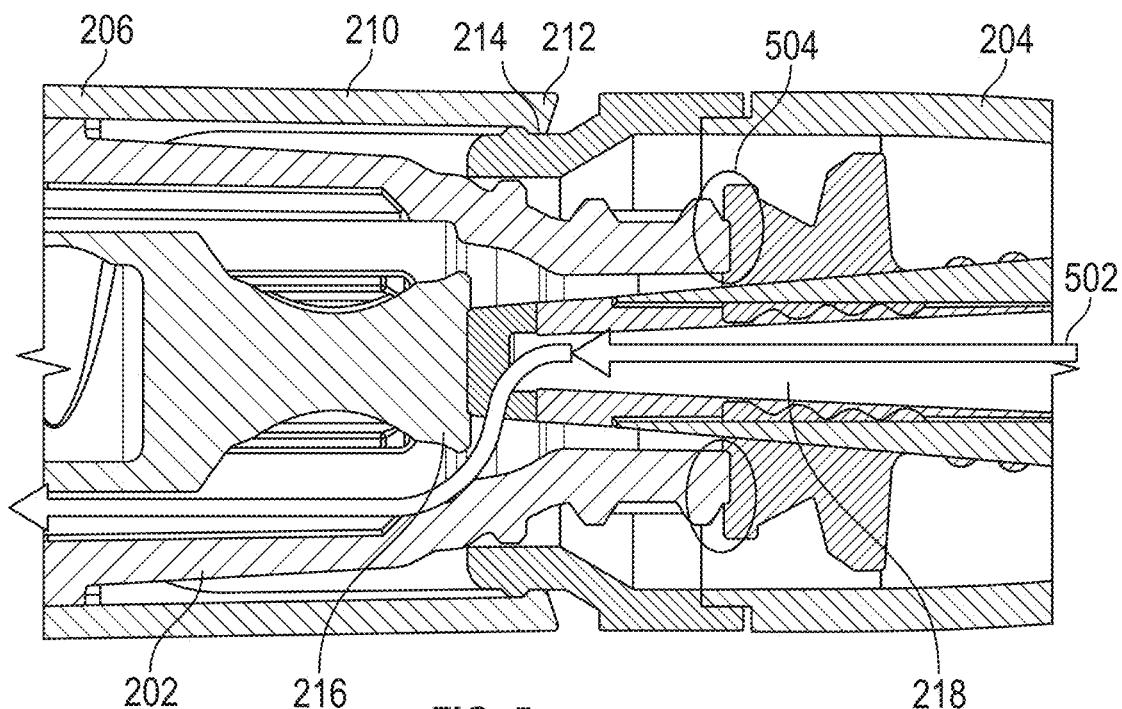
FIG. 5 shows a cross-sectional view of the coupler assembly of FIG. 2, with the first connector coupled to the second connector, in accordance with some embodiments of the present disclosure.

FIG. 5 shows a cross-sectional view of the coupler assembly 200 with the ring 206 coupled to first connector 202 and coupled to second connector 204, according to some embodiments of the present disclosure. When ring 206 is coupled to first connector 202 and second connector 204 simultaneously, such as shown in FIG. 5, first connector 202 and second connector 204 may be coupled together, creating a fluid flow path 502 through both connectors. This fluid flow path may be created when the fluid communication path between the first inlet and the first outlet of first connector 202 aligns with the fluid communication path between the first end and the second end of second connector 204.

In some embodiments, when first connector 202 and second connector 204 are coupled, a portion of first connector 202 may fit within a portion of second connector 204. First connector 202 and second connector 204 may fit together to create flow path seals 504. When first connector 202 and second connector 204 are not coupled, flexible valve 216 may extend to a far edge of first connector 202. When first connector 202 and second connector 204 are coupled, valve 218 may press against flexible valve 216, compressing flexible valve 216 such that the extension of flexible valve 216 ends within an interior portion of first connector 202.

In some embodiments, first connector 202 is connected to a first portion of tubing and second connector 204 is connected to a second portion of tubing. When first connector 202 is coupled to second connector 204, fluid may flow between the first portion of tubing through the coupled connectors and through the second portion of tubing.

Figure 6:
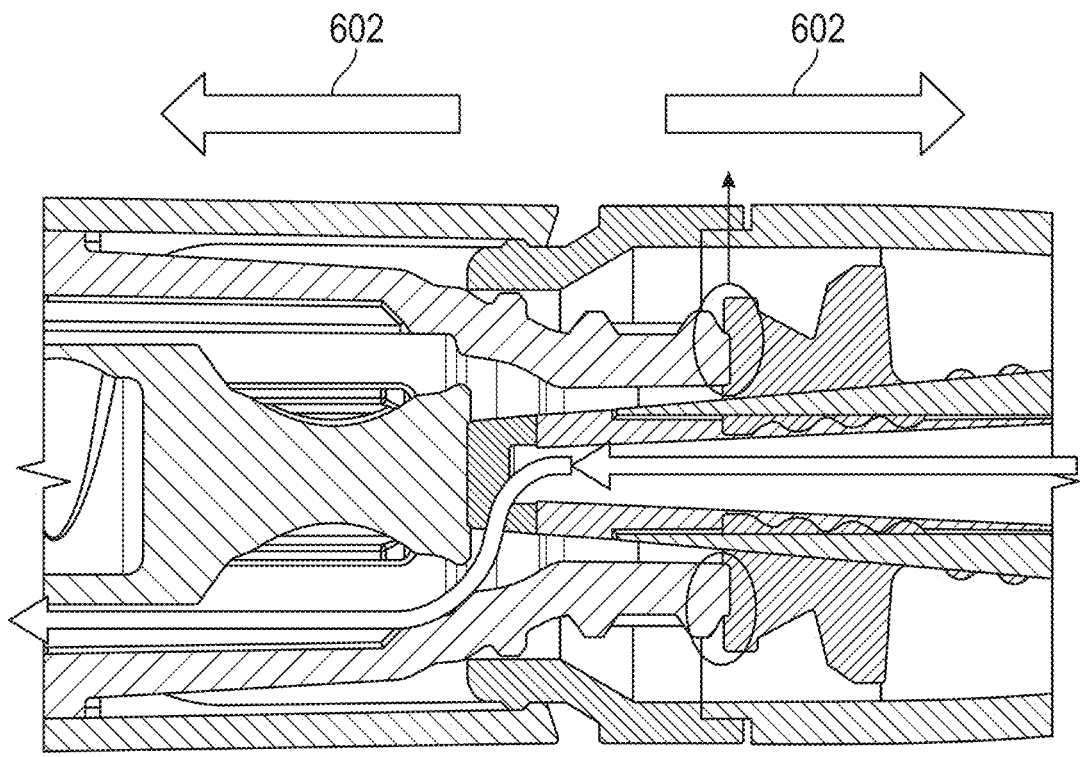
FIG. 6 shows the cross-sectional view of FIG. 5 with a decoupling force noted, in accordance with some embodiments of the present disclosure.

FIG. 6 shows the cross-sectional view of FIG. 5 as well as decoupling force 602, according to some embodiments of the present disclosure. Decoupling force 602 may decouple first connector 202 from second connector 204. Decoupling force 602 may pull first connector 202 away from second connector 204 or pull second connector 204 away from first connector 202. Decoupling force 602 may act along an axis that is central to first connector 202 and second connector 204 while they are coupled. Decoupling force 602 may be a resultant force acting along an axis central to first connector 202 and second connector 204 while they are coupled, or of a force that acts upon first connector 202 or upon second connector 204, or upon the first portion or tubing or upon the second portion of tubing.

Decoupling force 602 may decouple first connector 202 from second connector 204 when decoupling force 602 exceeds a predetermined threshold force. For example, if decoupling force 602 is less than the predetermined threshold force, first connector 202 may not decouple from second connector 204. The predetermined threshold force prevents inadvertent or accidental decoupling based on minor forces or movements. The predetermined threshold force may be based on the coupling of protrusions 212 into indentation 214. For example, arms 210 may be configured to releasably couple to second connector 204 and may allow for second connector 204 to decouple from ring 206 and first connector 202 when the decoupling force 602 exceeds the predetermined threshold force.

In some embodiments, the predetermined threshold force is approximately 5 pounds (lbs). The predetermined threshold force may be from approximately 1 lb to approximately 8 lbs, approximately 3 lbs to approximately 7 lbs, approximately 4 lbs to approximately 6 lbs, or greater than 8 lbs.

Figure 7:
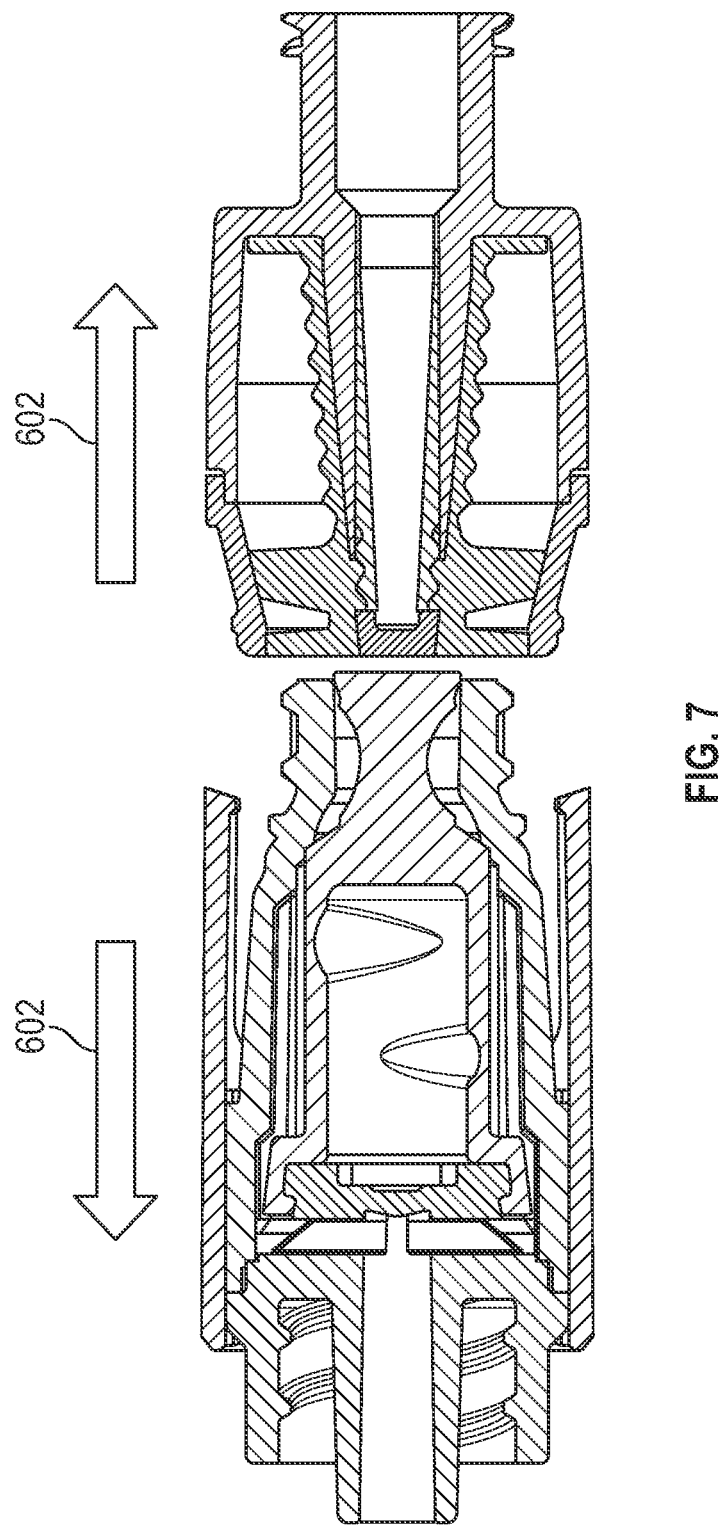
FIG. 7 shows a cross-sectional view of the coupler assembly of FIG. 6 after being decoupled, in accordance with some embodiments of the present disclosure.

FIG. 7 shows a cross-sectional view of the coupler assembly of FIG. 6 after being decoupled by decoupling force 602, in accordance with some embodiments of the present disclosure.

The disclosures described herein include at least the following clauses:

Clause 1. A coupler assembly comprising: a first connector having an outer surface and a first fluid pathway; a second connector having an exterior rim and a second fluid pathway; and a ring having a first portion and an axially offset second portion, the first portion being configured to be coupled to the outer surface of the first connector, and the second portion having a plurality of arms extending axially away from the first portion, wherein, when the ring is coupled to the first connector, and when the first and second connectors are coupled together such that the first fluid pathway is in fluid communication with the second fluid pathway, the plurality of arms are configured to detachably engage the exterior rim of the second connector to secure the coupling of the first and second connectors.

Clause 2. The coupler assembly of Clause 1, wherein each of the plurality of arms includes connecting portions which engage with the exterior rim of the second connector.

Clause 3. The coupler assembly of Clause 1, wherein the ring is configured to detach the first connector and the second connector upon a separating force exceeding a predetermined threshold force.

Clause 4. The coupler assembly of Clause 1, wherein the outer surface comprises an alignment detent, and the ring comprises an alignment tab, wherein the alignment tab is configured to be received by the alignment detent when the ring is coupled to the outer surface of the first connector.

Clause 5. The coupler assembly of Clause 1, wherein the plurality of arms is configured to detachably engage, via an interference fit, the exterior rim of the second connector.

Clause 6. The coupler assembly of Clause 3, wherein the plurality of arms and the exterior rim of the second connector are configured to detach upon a decoupling force exceeding a predetermined coupling force.

Clause 7. The coupler assembly of Clause 3, wherein the ring and the first connector are configured to detach upon a decoupling force exceeding a predetermined coupling force.

Clause 8. The coupler assembly of Clause 3, wherein the separating force is applied axially along the first connector and the second connector.

Clause 9. The coupler assembly of Clause 3, wherein the separating force is a resultant axial force along the coupled first connector and second connector.

Clause 10. The coupler assembly of Clause 1, wherein the first connector comprises an exterior portion and the second connector comprises an interior chamber such that the exterior portion of the first connector fits within the interior chamber of the second connector to provide fluid communication between the first and second fluid pathways.

Clause 11. A method of coupling two connectors comprising: providing a first connector with a first end and a second end opposite the first end; providing a second connector with an exterior rim; sliding a ring having a plurality of arms around the first connector; detachably connecting the ring to the first connector via a detent on the first connector and an engagement means on the ring; detachably connecting the ring to the second connector via the plurality of arms engaging with the exterior rim of the second connector; and forming a fluid pathway between the coupled first and second connectors.

Clause 12. The method of Clause 11, wherein the sliding the ring comprises sliding the ring around the first connector from the first end.

Clause 13. The method of Clause 11, wherein the sliding the ring comprises sliding the ring around the first connector from the second end.

Clause 14. The method of Clause 11, further comprising detaching the first connector and the second connector with an application of a force exceeding a predetermined threshold force.

Clause 15. The method of Clause 14, wherein the detaching the first connector and the second connector creates a break in the fluid pathway.

Clause 16. A coupling assembly, comprising: a first connector, including: a first connector body having a first inlet and a first outlet in fluid communication with the first inlet; and a collar sleeved over the first connector body between the first inlet and the first outlet, the collar comprising a collar body including a plurality of arms extending outward circumferentially from the collar body; and a second connector, including: a second connector body comprising a first end and a second end in fluid communication with the first end; wherein the collar body connects to an outer surface of the first connector via a friction or interference fit; and wherein the plurality of arms of the collar connects to an outer surface of the second connector via a friction or interference fit.

Clause 17. The coupling assembly of Clause 16, wherein the plurality of arms of the collar further comprises an interior ridge that connect to an exterior rim of the second connector to form the friction or interference fit.

Clause 18. The coupling assembly of Clause 17, wherein the interior ridge of the plurality of arms of the collar disengages from the exterior rim of the second connector upon an application of a force exceeding a predetermined threshold force.

Clause 19. The coupling assembly of Clause 18, wherein the force exceeding a predetermined threshold force is applied such that the first connector is pulled away from the second connector.

Clause 20. The coupling assembly of Clause 16, wherein the first connector is coupled to a first portion of tubing at the first inlet, and the second connector is coupled to a second portion of tubing at the second end.

Clause 21. The coupling assembly of Clause 18, wherein a fluid flow exists between the first connector and the second connector when they are connected by the collar, and wherein the fluid flow is stopped by a self-sealing arrangement when the first connector and the second connector are disengaged.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A coupler assembly comprising:
    a first connector having an outer surface, a first end and a first fluid pathway;
    a second connector having an exterior rim, a second end and a second fluid pathway; and
    a ring having a first portion and an axially offset second portion, the first portion being configured to be coupled to the outer surface of the first connector, and the second portion having a plurality of arms extending axially away from the first portion,
    wherein, when the ring is coupled to the first connector from the first end of the first connector, and when the first end of the first connector and the second end of the second connector are coupled together such that the first fluid pathway is in fluid communication with the second fluid pathway, the plurality of arms are configured to detachably engage the exterior rim of the second end of the second connector to secure the coupling of the first and second connectors.

2. The coupler assembly of claim 1, wherein each of the plurality of arms includes connecting portions which engage with an indentation in the exterior rim of the second end of the second connector.

3. The coupler assembly of claim 1, wherein the ring is configured to detach the first connector and the second connector upon a separating force exceeding a predetermined threshold force.

4. The coupler assembly of claim 3, wherein the plurality of arms and the exterior rim of the second connector are configured to detach upon a decoupling force exceeding a predetermined decoupling force.

5. The coupler assembly of claim 3, wherein the ring and the first connector are configured to detach upon a decoupling force exceeding a predetermined decoupling force.

6. The coupler assembly of claim 3, wherein the separating force is applied axially along the first connector and the second connector.

7. The coupler assembly of claim 3, wherein the separating force is a resultant axial force along the coupled first connector and second connector.

8. The coupler assembly of claim 1, wherein the outer surface comprises an alignment detent, and the ring comprises an alignment tab, wherein the alignment tab is configured to be received by the alignment detent when the ring is coupled to the outer surface of the first connector.

9. The coupler assembly of claim 1, wherein the plurality of arms is configured to detachably engage, via an interference fit, the exterior rim of the second connector.

10. The coupler assembly of claim 1, wherein the first connector comprises an exterior portion and the second connector comprises an interior chamber such that the exterior portion of the first connector fits within the interior chamber of the second connector to provide fluid communication between the first and second fluid pathways.

11. A method of coupling two connectors comprising:
providing a first connector of the two connectors with a first end and a second end opposite the first end;
providing a second connector of the two connectors with an exterior rim and having a third end and a fourth end opposite the third end;
sliding a ring having a plurality of arms around the first end of the first connector;
detachably connecting the ring to the first connector via a detent on the first connector and an engagement means on the ring;
detachably connecting the ring to the second connector via the plurality of arms engaging with the exterior rim of the third end of the second connector; and
coupling the second end of the first connector with the third end of the second connector to form a fluid pathway between the coupled first and second connectors.

12. The method of claim 11, further comprising detaching the first connector and the second connector with an application of a force exceeding a predetermined threshold force.

13. The method of claim 12, wherein the detaching the first connector and the second connector creates a break in the fluid pathway.

14. A coupling assembly, comprising:
a first connector, including:
a first connector body having a first inlet and a first outlet in fluid communication with the first inlet; and
a collar sleeved past the first inlet and over the first connector body between the first inlet and the first outlet, the collar comprising a collar body including a plurality of arms extending outward circumferentially from the collar body; and
a second connector, including:
a second connector body comprising a first end and a second end in fluid communication with the first end;
wherein the collar body connects to an outer surface of the first connector via a friction or interference fit; and
wherein the plurality of arms of the collar connects to an outer surface of the first end of the second connector via a friction or interference fit when the first end of the second connector is coupled to the first outlet of the first connector.

15. The coupling assembly of claim 14, wherein the plurality of arms of the collar further comprises an interior ridge that connect to an exterior rim of the second connector to form the friction or interference fit.

16. The coupling assembly of claim 15, wherein the interior ridge of the plurality of arms of the collar disengages from the exterior rim of the second connector upon an application of a force exceeding a predetermined threshold force.

17. The coupling assembly of claim 16, wherein the force exceeding the predetermined threshold force is applied such that the first connector is pulled away from the second connector.

18. The coupling assembly of claim 16, wherein a fluid flow exists between the first connector and the second connector when they are connected by the collar, and wherein the fluid flow is stopped by a self-sealing arrangement when the first connector and the second connector are disengaged.

19. The coupling assembly of claim 14, wherein the first connector is coupled to a first tubing line at the first inlet, and the second connector is coupled to a second tubing line at the second end.

* * * * *